(12) United States Patent  (10) Patent No.: US 8,591,233 B2
Arai et al.  (45) Date of Patent: Nov. 26, 2013

(54) DENTURE ATTACHMENT

(75) Inventors: Kazuo Arai, Aichi (JP); Yoshinobu Honkura, Aichi (JP); Yasuhiro Takeuchi, Aichi (JP)

(73) Assignee: Aichi Steel Corporation, Tokai-shi (JP)

( * ) Notice: Subject to any disclaimer, the term of this patent is extended or adjusted under 35 U.S.C. 154(b) by 0 days.

(21) Appl. No.: 13/642,303

(22) PCT Filed: Apr. 15, 2011

(86) PCT No.: PCT/JP2011/059374
§ 371 (c)(1),
(2), (4) Date: Oct. 19, 2012

(87) PCT Pub. No.: WO2011/132607
PCT Pub. Date: Oct. 27, 2011

(65) Prior Publication Data
US 2013/0034831 A1  Feb. 7, 2013

(30) Foreign Application Priority Data
Apr. 19, 2010  (JP) ................................. 2010-095783

(51) Int. Cl.
*A61C 13/235* (2006.01)
(52) U.S. Cl.
USPC ....................................................... 433/189
(58) Field of Classification Search
USPC ................... 433/172–176, 189, 199.1, 201.1
See application file for complete search history.

(56) References Cited

U.S. PATENT DOCUMENTS

| | | | |
|---|---|---|---|
| 6,652,278 B2 | 11/2003 | Honkura et al. | |
| 6,709,270 B2 | 3/2004 | Arai et al. | |
| 2002/0137010 A1 | 9/2002 | Honkura et al. | |
| 2003/0059740 A1 | 3/2003 | Honkura et al. | |
| 2003/0118969 A1 | 6/2003 | Arai et al. | |
| 2006/0160048 A1 | 7/2006 | Honkura et al. | |
| 2007/0037124 A1 | 2/2007 | Honkura et al. | |

FOREIGN PATENT DOCUMENTS

| | | |
|---|---|---|
| JP | 7 136190 | 5/1995 |
| JP | 10 229992 | 9/1998 |
| JP | 2001 37781 | 2/2001 |
| JP | 2001 321393 | 11/2011 |
| WO | 2004 082513 | 9/2004 |
| WO | 2005 023140 | 3/2005 |

OTHER PUBLICATIONS

International Search Report Issued on Jun. 7, 2011 in PCT/JP11/059374 Filed Apr. 15, 2011.

*Primary Examiner* — Todd Manahan
*Assistant Examiner* — Michael R Ballinger
(74) *Attorney, Agent, or Firm* — Oblon, Spivak, McClelland, Maier & Neustadt, L.L.P.

(57) ABSTRACT

A magnetic device includes a cylindrical portion and a flange portion. The cylindrical portion is mounted with a cylindrical shaped flexible sleeve. The sleeve is axially longer than the cylindrical portion and includes an outer peripheral concavo-convex portion. When one end of the sleeve is abutted on a flange portion, the other end of the sleeve is projected above an attractive surface to form a keeper housing recess. The sleeve is relatively moved in an axial direction of the magnetic device to be inserted into and removed from a top end of the cylindrical portion. The magnetic device is used under condition the sleeve is fitted, an outer side surface of the magnetic device including the outer peripheral concavo-convex portion of the sleeve and the flange portion abutted on the one end of the sleeve is embedded in a denture base, and the keeper housing recess is exposed.

8 Claims, 8 Drawing Sheets

DENTURE ATTACHMENT

FIELD OF THE INVENTION

The invention relates to a denture attachment that fixes a denture in the mouth using magnetic attractive force.

BACKGROUND OF THE INVENTION

In the field of odontotherapy were so far developed various types of denture attachments using magnetic attractive force to readily attach and detach a denture, an example of which is disclosed in Patent Reference 1. Conventionally, the denture attachment includes a magnetic device provided in a denture base to which the denture is fixed and exerting magnetic attractive force, and a keeper provided in an abutment (remaining teeth or implant) and made of a soft magnetic material.

PRIOR ART DOCUMENT

Patent Reference

Patent Reference 1: Japanese Patent Application Publication No. 07-136190
Patent Reference 2: Japanese Patent Application Publication No. 2001-321393

SUMMARY OF THE INVENTION

Problems to be solved by the Invention

The denture attachment using the magnetic attractive force (hereinafter referred to as a magnetic attachment) is readily attachable and detachable and allowed to have a slight sideslip on surfaces of the magnetic device and the keeper abutted to each other (attractive surface and attracted surface). Therefore, a lateral force applied to the abutment holding the keeper escapes to protect the abutment. Particularly, magnetic attachments, which are devised to deal with an implant increasingly widespread in recent years, are designed to reduce a lateral force applied to the implant. Therefore, the number of required implants to be embedded may be reduced.

In consequence of the sideslip generated between the magnetic device and the keeper, the denture may be disengaged. This is conceivable that a relatively large lateral force causes the sideslip and relative rotation in a direction where abutment surfaces of the magnetic device and the keeper are pulled away from each other diagonally. For the purpose of solving the aforementioned problem, the magnetic device and the keeper may be shaped to be in mesh with each other so as to avoid the sideslip and the relative rotation.

An example of the technical option is disclosed in Patent Reference 2. In this technique, a guide ring made of a non-magnetic metal is welded and secured to a circumferential part of a magnetic structure, and the guide ring and a projected portion of the keeper are fitted with each other as illustrated in FIG. 1. Another structural example is to form a projected portion in the keeper and a dented portion in the magnetic structure for the projection to be fitted in so that these portions are fitted with each other.

These structures, however, practically disallow any sideslip between the magnetic device and the keeper, thereby losing most of the lateral force reducing effect which is an advantage of any magnetic attachments. These magnetic attachments, therefore, were so far applied to patients whose abutments were in good condition.

To solve these conventional technical problems, the invention provides a denture attachment that accomplishes a lateral force reducing effect and a denture disengagement controlling effect which are particular advantages of any magnetic attachments.

Means for Solving Problems

A denture attachment according to the invention includes a magnetic device provided in a denture base to exert magnetic attractive force, and a keeper made of a soft magnetic material and provided in an abutment. An attractive surface of the magnetic device and an attracted surface of the keeper are abutted and joined to each other by the magnetic attractive force. The magnetic device has a permanent magnet embedded in the magnetic device, and includes a cylindrical portion having a cylindrical outer shape and provided with the attractive surface in a top end of the cylindrical portion, and a flange portion projected radially outward in a rear end of the cylindrical portion. The cylindrical portion is mounted with a sleeve from a top end side thereof, the sleeve having flexibility and formed in a cylindrical shape. The sleeve has an outer peripheral concavo-convex portion projected radially outward or dented radially inward on an outer peripheral surface, an axial length longer than the cylindrical portion, and one end part projecting above the attractive surface while having the other end part abutted on the flange portion so as to define a keeper housing recess surrounded by the sleeve and the attractive surface. The sleeve is configured to be relatively moved in an axial direction of the magnetic device to be inserted into and removed from a top end of the cylindrical portion. The magnetic device is configured to be used under the condition that the sleeve is fitted, and an outer side surface of the magnetic device including the outer peripheral concavo-convex portion of the sleeve and the flange portion abutted on the one end part of the sleeve is embedded in the denture base, while having the keeper housing recess exposed.

Effects of the Invention

The magnetic device of the denture attachment according to the invention in use is embedded in the denture base with the flexible sleeve being mounted on the cylindrical portion. The keeper is housed in the keeper housing recess surrounded by the sleeve and the attractive surface, and the attractive surface on the top end of the cylindrical portion and the attracted surface of the keeper are abutted to establish an attractive state by magnetic attractive force. In this state, the sleeve encompasses an outer side surface of the keeper.

The sleeve is made of a flexible material. When a lateral force is applied to the denture, therefore, the sideslip between the magnetic device and the keeper relative to each other is allowed by the clearance between the sleeve and the keeper, and elastic deformability of the sleeve, thus providing the effect of reducing the lateral force.

In the case where a relative rotational force is generated in the direction to diagonally force the respective abutment surfaces of the keeper and the magnetic device (attractive surface and attracted surface) apart from each other, such a movement is arrested by the sleeve surrounding the outer side surface of the keeper. This may suppress a chance of disengagement of the denture compared to the related art.

The magnetic device and the keeper made of metallic materials are basically usable nearly permanently. However, the sleeve made of the flexible material (resin or rubber) may be worn or degraded. Therefore, it is preferable to replace the sleeve with a new one on a regular basis. The sleeve is configured to be relatively moved in the axial direction of the magnetic device so as to be inserted into and removed from the top end of the cylindrical portion. This demands no particular expertise of dental technicians, allowing dentists themselves to replace the sleeve during dental treatments. The removal of the magnetic device from the denture base, which is a necessary step for replacement of the sleeve, can be handled during periodical adjustments of the denture base performed as a part of dental treatments.

It is unnecessary to use any jig or tool to fit and remove the sleeve to and from the magnetic device. After embedded in the denture base, the outer peripheral concavo-convex portion of the sleeve serves as an undercut in the denture base, helping to securely locate the sleeve in the denture base. Further, one end of the sleeve is abutted on the flange portion of the magnetic device so that the flange portion is firmly held between the sleeve and the denture base. The magnetic device and the sleeve are thus combined as an integral unit and securely located in the denture base. This prevents the magnetic device or the sleeve from being accidentally disengaged from the denture base when the denture attachment is in use.

As described so far, the denture attachment according to the invention is structurally advantageous in that the lateral force and the denture disengagement are effectively controlled by characteristics of the flexible sleeve, and replacement of the used sleeve with a new one to maintain such great advantages can be performed during dental treatments.

MODE FOR CARRYING OUT THE INVENTION

The sleeve of the denture attachment according to the invention is made of any known material with flexibility such as a resin or rubber. For example, POM (polyacetal) may be used.

The outer peripheral concavo-convex portion of the sleeve may be formed in various shapes, for example, a flange-like shape projected radially outward, a groove-like portion dented radially inward, and a combination thereof.

Preferably, the cylindrical portion of the magnetic device has a tapered section in a top end-side outer peripheral part of the cylindrical portion, which is diametrically reduced toward the attractive surface, and the sleeve has a chamfered section in an inner peripheral corner part of the one end part. These tapered section and chamfered section make it easier for the sleeve to be mounted on the cylindrical portion.

Preferably, the keeper has an outer diameter larger than an outer diameter of the cylindrical portion, and the sleeve has a base section covering an outer peripheral surface of the cylindrical portion while having the one end part abutted on the flange portion, and a projection where the keeper housing recess is formed, the projection having an inner diameter larger than an inner diameter of the base section. In this case, the whole attractive surface of the magnetic device is easily abutted on the attracted surface of the keeper, and an adsorbing strength is hardly weakened by the sideslip generated between the magnetic device and the keeper.

Preferably, the inner diameter of the base section of the sleeve is adjusted relative to the outer diameter of the cylindrical portion in the magnetic device so that the sleeve can be fitted with an appropriate pressing force. It is preferable to set, for example, an inner diameter difference from about 0.01 mm to 0.3 mm as a press-fitting allowance.

The press-fitting configuration is not limited even if the press-fitting allowance is omitted or a very small clearance is provided so far as the base section and the sleeve are kept engaged with each other by the assistance of, for example, a surface frictional force.

The inner diameter of the projected portion of the sleeve is preferably adjusted to a dimension including a minimal clearance corresponding to the outer diameter of the keeper. The clearance is preferably set to about 0.05 mm to 1.0 mm.

Preferably, the keeper is provided in a top end of an implant embedded in a jawbone. This effectively reduces the lateral force applied to the implant. It is effective for protection of the implant and reduction of the number of required implants.

EMBODIMENT

Embodiment 1

A denture attachment according to an embodiment of the invention is described referring to FIGS. 1 to 12.

Figure 1:
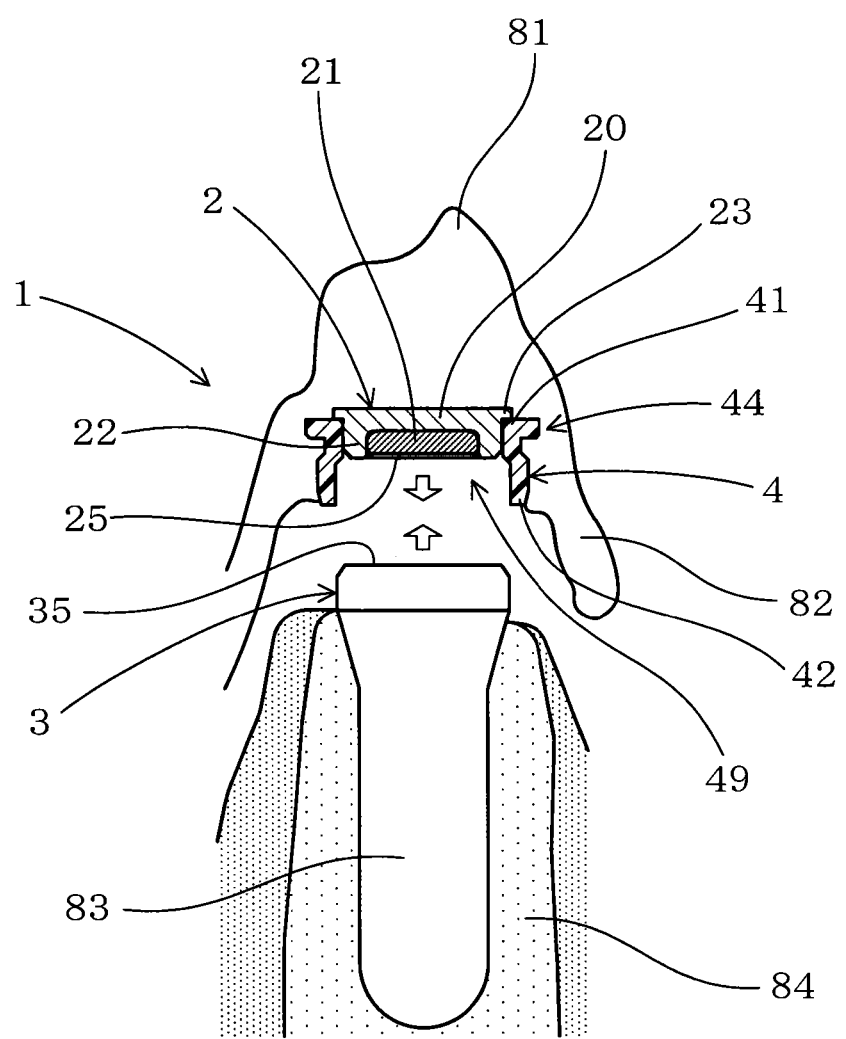
FIG. 1 is an illustration of structural characteristics of a denture attachment according to an embodiment 1 of the invention, in which a magnetic device and a keeper are separated from each other.
Figure 2:
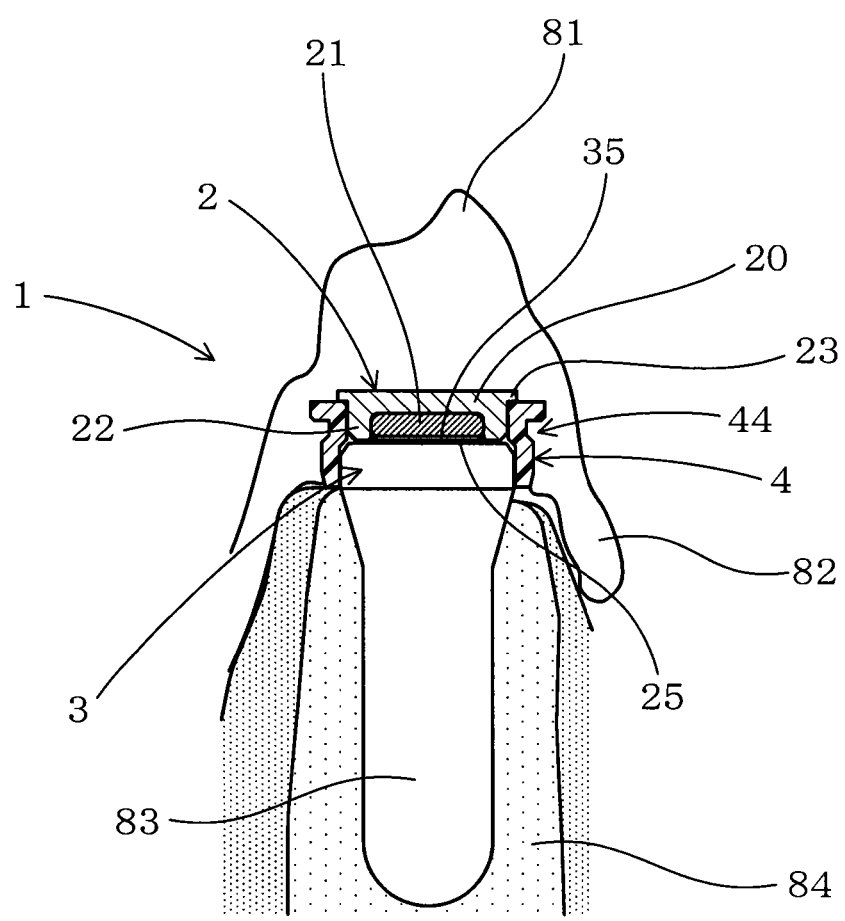
FIG. 2 is an illustration of structural characteristics of the denture attachment according to the embodiment 1, wherein the magnetic device and the keeper are fitted to each other.

As illustrated in FIGS. 1 and 2, a denture attachment 1 according to the embodiment has a magnetic device 2 provided in a denture base 82 of a denture 81 to exert magnetic attractive force, and a keeper 3 made of a soft magnetic material and provided in an implant 83 serving as an abutment. When an attractive surface 25 of the magnetic device 2 and an attracted surface 35 of the keeper 3 are abutted on each other, these surfaces are attracted to each other by magnetic attractive force.

As illustrated in FIGS. 1 to 5, the magnetic device 2 is embedded with a permanent magnet 21 and includes a cylindrical portion 22 having the attractive surface 25 on a top end thereof and formed in a cylindrical outer shape, and a flange portion 23 projected radially outward in a rear end of the cylindrical portion 22.

The cylindrical portion 22 is mounted with a sleeve 4 having flexibility and formed in a cylindrical shape from a top end side thereof. The sleeve 4 is formed in a larger axial length than the cylindrical portion 22 and has an outer peripheral concavo-convex portion 44 projected radially outward and dented radially inward on an outer peripheral surface thereof, and one end part 42 of the sleeve 4 is projected above the attractive surface 25 while having another one end part 41 of the sleeve 4 abutted on the flange portion 23 to form a keeper housing recess 49 surrounded by the sleeve 4 and the attractive surface 25.

The sleeve 4 is relatively moved in an axial direction of the magnetic device 2 to be inserted into and removed from a top end the cylindrical portion 22.

As illustrated in the drawing, the magnetic device 2 is used under the condition that the sleeve 4 is fitted, an outer surface of the magnetic device 2 including the outer peripheral concavo-convex portion 44 of the sleeve 4 and the flange portion 23 abutted on the one end part 41 of the sleeve 4 is embedded in the denture base 82, and the keeper housing recess 49 is exposed.

Hereinafter the embodiment will be described in further detail.

Figure 3:
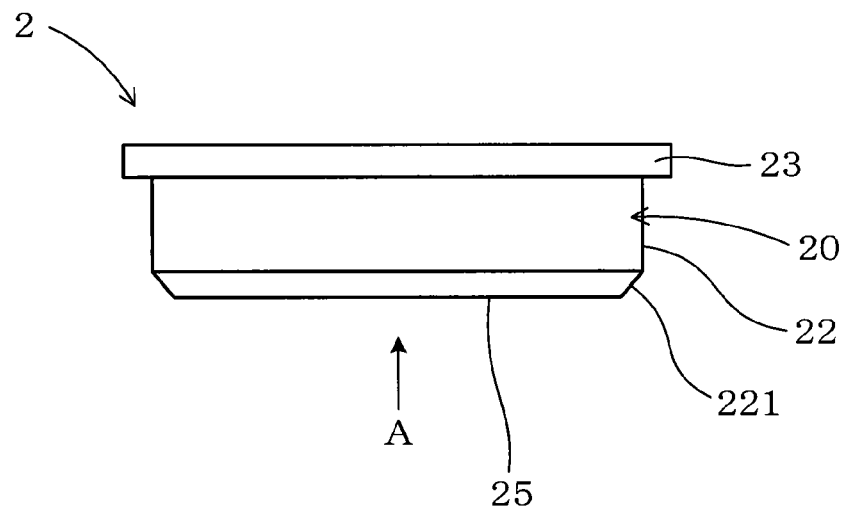
FIG. 3 is a front view of the magnetic device according to the embodiment 1.
Figure 4:
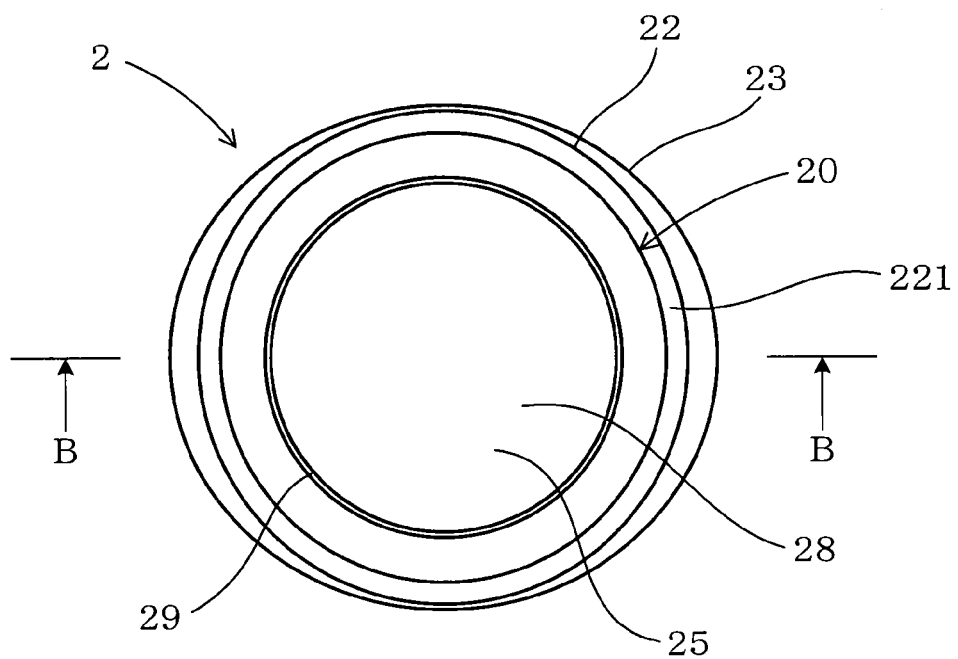
FIG. 4 is a plan view of the magnetic device according to the example 1 (when viewed as illustrated with arrow A of FIG. 3).
Figure 5:
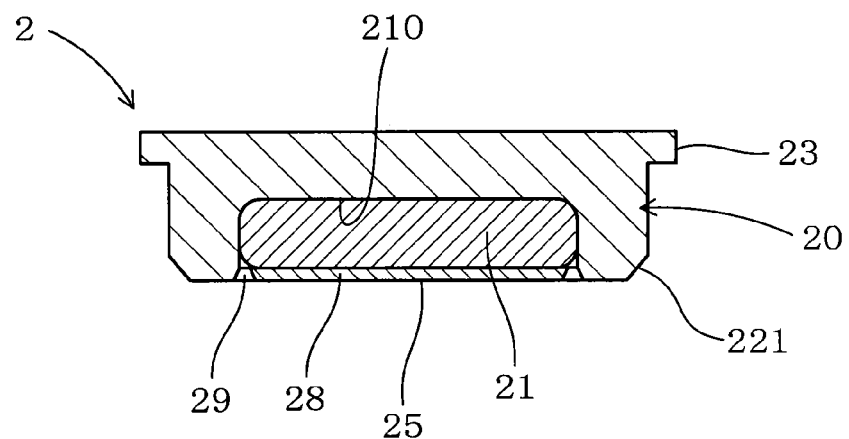
FIG. 5 is a sectional view of the magnetic device according to the embodiment 1 (when viewed in cross section cut along B-B of FIG. 4).

As illustrated in FIGS. 3 to 5, the magnetic device 2 has a yoke 20 made of a soft magnetic material and having a recess 210 that houses the permanent magnet 21 exerting the magnetic attractive force, and a disc 28 made of a soft magnetic material and joined with the yoke 20 so as to seal an opening of the recess 210 in which permanent magnet 21 is placed. The disc 28 and the yoke 20 are welded to each other in a welding portion 29.

The yoke 20 has an overall shape similar to a disc shape, and includes the cylindrical portion 22 and the flange portion 23 projected radially outward in a rear end thereof. According to the embodiment, the flange portion 23 has an elliptical outer shape as illustrated in FIG. 4. The flange portion 23 is projected by 0.25 mm corresponding to the length of the major axis of the elliptical shape and by 0.05 mm corresponding to the length of the minor axis of the elliptical shape. The elliptical shape is intended to prevent the magnetic device 3 from circumferentially rotating upon embedding in the denture base 82.

A part of the cylindrical portion 22 mounted with the sleeve 4 has an outer-diametrically equal straight shape. Further, the cylindrical portion 22 has a tapered section 221 diametrically reduced toward the attractive surface 25 in a top end-side outer peripheral part thereof. The tapered section 221 and a chamfered section 412 of the sleeve 4 described later make it easier for the sleeve 4 to be mounted on the cylindrical portion 22 of the magnetic device 2.

To produce the yoke 20, a soft magnetic material, 19Cr-2Mo-0.2Ti—Fe, was subjected to the cutting work. The disc 28 is also produced from a circular plate made of the soft magnetic material, 19Cr-2Mo-0.2Ti—Fe. The welding portion 29 is produced from a non-magnetic material.

Figure 6:
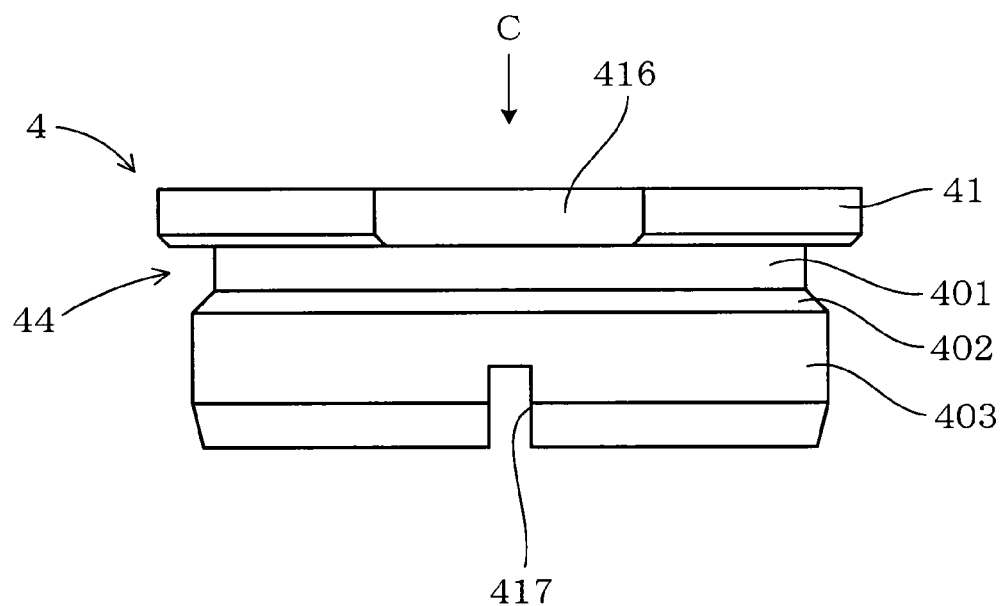
FIG. 6 is a front view of a sleeve according to the embodiment 1.
Figure 7:
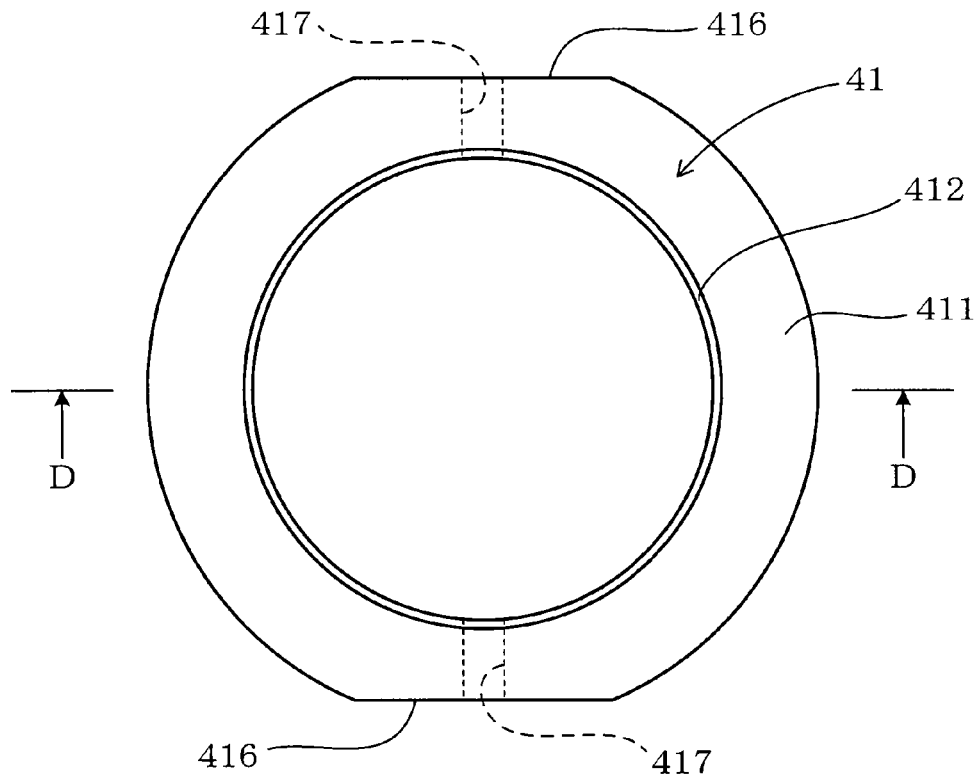
FIG. 7 is a plan view of the sleeve according to the embodiment 1 (when viewed as illustrated with arrow C of FIG. 6).
Figure 8:
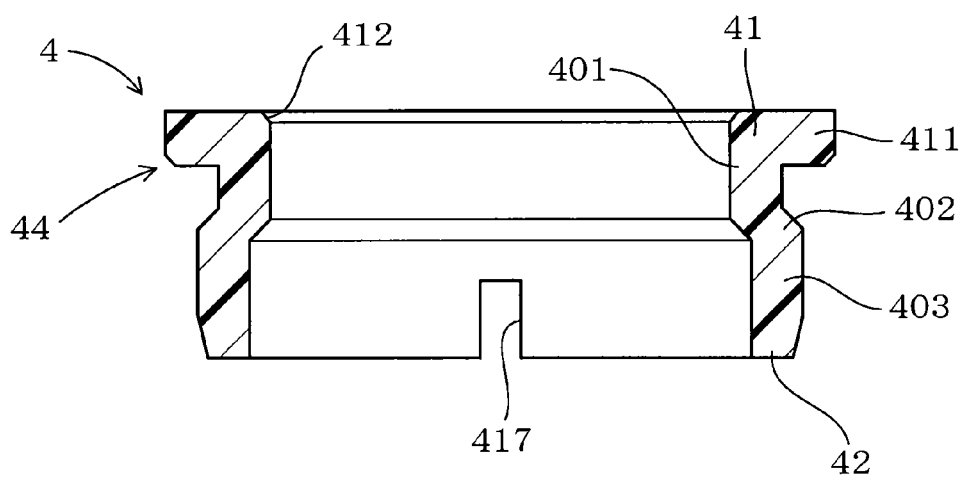
FIG. 8 is a sectional view of the sleeve according to the embodiment 1 (when viewed in cross section taken along D-D in FIG. 7).

As illustrated in FIGS. 6 to 8, the sleeve 4 has an almost cylindrical overall shape, and includes a base section 401 which covers an outer peripheral surface of the cylindrical portion 22 when the sleeve 4 is mounted on the cylindrical portion 22, and a projection 403 where the keeper housing recess 49 is formed. The projection 403 has an inner diameter larger than an inner diameter of the base section 401 in regard to an outer diameter of the keeper 3 larger than an outer diameter of the cylindrical portion 22 of the magnetic device 2. Between the base section 401 and the projection 403 is formed a sleeve tapered section 402 having inner and outer diameters gradually changed.

A sleeve flange section 411 projected radially outward is formed on an outer peripheral surface of the one end part 41 abutted on the flange portion 23 when the base section 401 of the sleeve 4 is fitted to the cylindrical portion 22. The outer peripheral concavo-convex portion 44 is formed as a result of radial dimensional changes of the sleeve flange section 411 and the sleeve tapered section 402.

A chamfered section 412 is formed in an inner peripheral corner part in the one end part 41 of the sleeve 4. This makes it easier for the sleeve 4 to be mounted on the cylindrical portion 22 of the magnetic device 2 together with the tapered section 221 of the cylindrical portion 22. In two circumferential positions of the sleeve flange section 411 were provided notches 416 formed by linearly cutting circular parts to assist a smooth flow of dental resin which will be described later. The inner diameter of the base section 401 of the sleeve 4 was set to 4.33 mmφ in view of the press-fitting allowance of 0.07 mm.

At two positions in a top end of the projection 403 of the sleeve 4, groove sections 417 radially penetrating through are formed. When the dental resin is injected through the groove sections 417 and solidified, the sleeve 4 is surely prevented from circumferentially rotating in the denture base 82. The groove sections 417 may be formed at any positions in the circumferential direction, and there may be one groove section 417 or a plurality of groove sections 417. The notches 416 serve to prevent the sleeve 4 from rotating similarly to the groove sections 417. According to the embodiment, the groove sections 417 and the notches 416 are formed at circumferentially equal positions, however, these sections may be formed at random positions in the circumferential direction.

The material used to produce the sleeve 4 is POM (polyacetal).

As illustrated in FIGS. 1 and 2, the present example used the implant 83 embedded in a jawbone 84 as an abutment and provided the keeper 3 made of a soft magnetic material in the plant 83. The outer diameter of the keeper 3 was 4.75 mmφ, the inner diameter of the projection 403 of the sleeve 4 was 5.13 mmφ, and a clearance provided between the sleeve 4 and the keeper 3 was 0.38 mm.

Hereinafter, operational advantages of the denture attachment 1 according to the embodiment will be described.

As illustrated in FIGS. 1 and 2, the magnetic device 2 of the denture attachment 1 in use is embedded in the denture base 82 with the flexible sleeve 4 being mounted on the cylindrical portion 22. Then, the keeper 3 is housed in the keeper housing recess 49 surrounded by the sleeve 4 and the attractive surface 25, and the attractive surface 25 on the top end of the cylindrical portion 22 and the attracted surface 35 of the keeper 3 are abutted and attracted to each other by magnetic attractive force. In the described state, the sleeve is surrounding the outer side surface of the keeper (FIG. 2).

The sleeve 4 is made of a flexible material. When a lateral force is applied to the denture 81, therefore, the sideslip between the magnetic device 2 and the keeper 3 relative to each other is allowed by the clearance between the sleeve 4 and the keeper 3, and elastic deformability of the sleeve 4, thus providing the effect of reducing the lateral force.

In the case where a relative rotational force is generated in the direction to diagonally force the respective abutment surfaces of the keeper 3 and the magnetic device 2 (attractive surface 25 and attracted surface 35) apart from each other, such a movement is arrested by the sleeve 4 surrounding the outer side surface of the keeper 3. This may suppress a chance of disengagement of the denture compared to the related art.

The magnetic device 2 and the keeper 3 made of metallic materials are basically usable nearly permanently. However, the sleeve 4 made of the flexible material may be worn or degraded. Therefore, it is preferable to replace the sleeve 4 with a new one on a regular basis. The sleeve 4 is configured to be relatively moved in an axial direction of the cylindrical portion 22 of the magnetic device 2 so as to be inserted into and removed from the top end of the cylindrical portion 22. This demands no particular expertise of dental technicians, allowing dentists themselves to replace the sleeve during dental treatments. The removal of the magnetic device from the denture base, which is a necessary step for replacement of the sleeve, can be handled during periodical adjustments of the denture base (rebasing) performed as a part of dental treatments.

The replacement of the sleeve 4 may be performed as described below.

Figure 9:
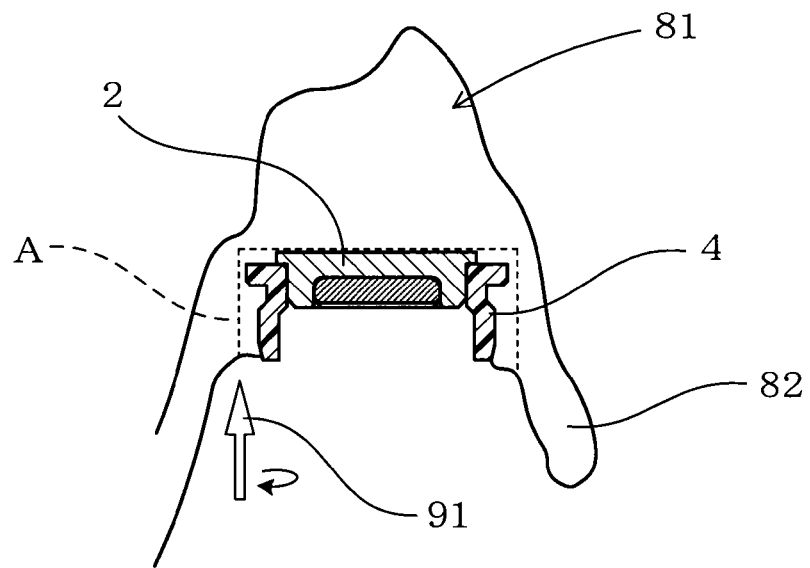
FIG. 9 is an illustration of a method of removing the magnetic device from a denture base according to the embodiment 1.

As illustrated in FIG. 9, a part of the denture base is drilled by a dental tool 91 or the like from the back side of the denture 81 during a dental treatment. For example, an area shown with a broken line A is drilled to reach the magnetic device 2 mounted with the sleeve 4.

Figure 10:
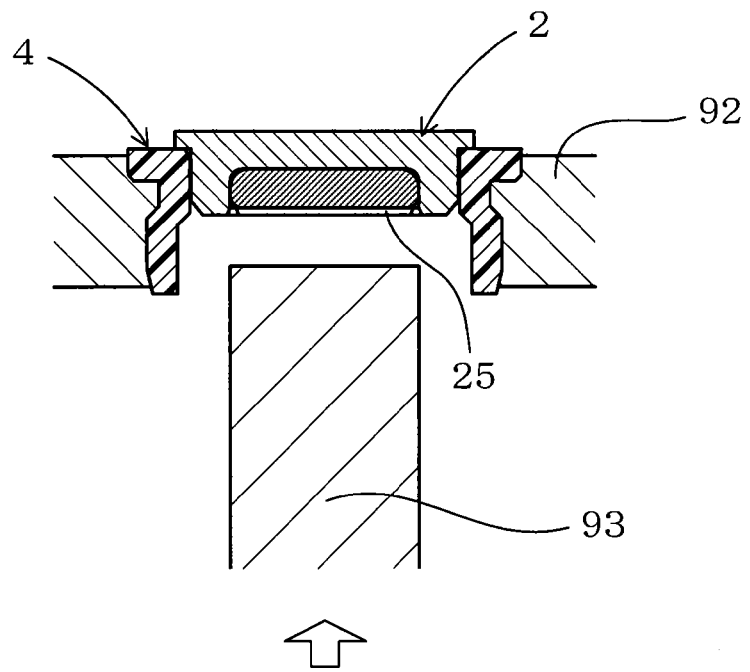
FIG. 10 is an illustration of a method of separating the magnetic device and the sleeve from each other according to the embodiment 1.

As illustrated in FIG. 10, the outer peripheral surface of the sleeve 4 mounted on the reached magnetic device 2 is held by a holding tool 92 separately prepared. Then, the attractive surface 25 of the magnetic device 2 is pushed axially by a bar member 93 having a diameter smaller than the inner diameter of the sleeve 4, and the magnetic device 2 is pulled out from the sleeve 4. The magnetic device and the sleeve 4 are thus easily separable from each other. The sleeve 4 separated from the magnetic device 2 is discarded.

Figure 11:
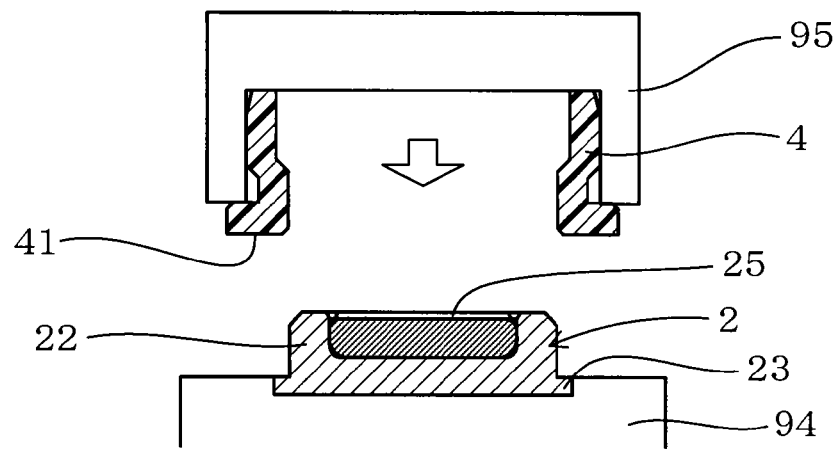
FIG. 11 is an illustration of a method of loading the magnetic device with a new sleeve according to the embodiment 1.

As illustrated in FIG. 11, the magnetic device 2 washed and disinfected is placed on a placement table 94 with the attractive surface 25 directed upward. A new sleeve 4 held by the holing tool 95 is moved in the axial direction of the cylindrical portion 22 of the magnetic device 2 and press fitted into the cylindrical portion 22 from the one end part 41. When the one end part 41 is abutted on the flange portion 23, the sleeve 4 is successfully fitted.

Figure 12:
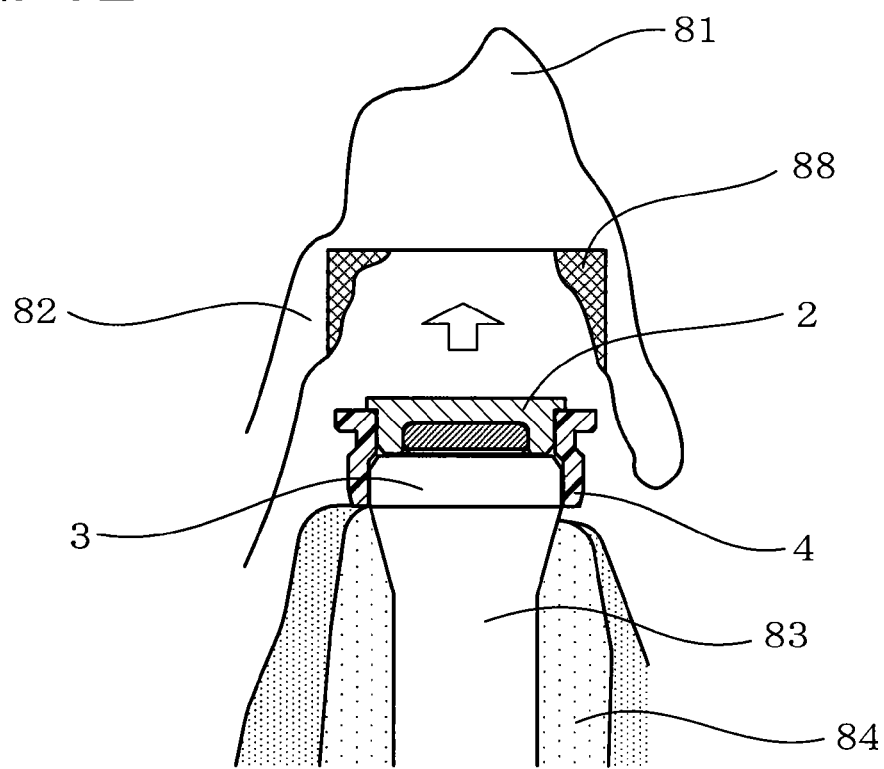
FIG. 12 is an illustration of a method of embedding the magnetic device mounted with the sleeve in the denture base according to the embodiment 1.

Next, the magnetic device 2 mounted with the sleeve 4 is embedded in the denture base 82 of the denture 81. As illustrated in FIG. 12, the attractive surface 25 of the magnetic device 2 mounted with the sleeve 4 is abutted on the attracted surface 35 of the keeper 3 currently used in the implant 83 of the mouth so that these surfaces are joined through the magnetic attractive force. As illustrated in the drawing, the magnetic device 2 mounted with the sleeve 4 and the keeper 3 are engaged with each other in the same manner as they are in practical use.

As illustrated in the drawing, a dental resin 88 is injected into a hole of the denture base 82 of the denture 81 from which the magnetic device 2 has been reached. Then, the denture 81 is mounted on the magnetic device 2, and the magnetic device 2 is inserted into the hole of the denture base 82 so that the dental resin 88 spreads around the magnetic device 2 and the sleeve 4. The inflow of the dental resin 88 is assisted by the notches 416 formed at two circumferential positions in the sleeve flange section 411 of the sleeve 4.

The dental resin 88 is cured to complete the rebasing of the denture 81 is completed.

The magnetic device 2 is provided in a denture base 82 of a new denture 81 in almost the same manner as described above.

In the denture 81 thus obtained, the outer peripheral concavo-convex portion 44 of the sleeve 4 serves as an undercut in the denture base, helping fixation of the sleeve 4 in the denture base 82. Further, the one end part 41 of the sleeve 4 is abutted on the flange portion 23 of the magnetic device 2 so that the flange portion 23 is gripped between the sleeve 4 and the denture base 82. The magnetic device 2 and the sleeve 3 thus integrally combined are securely located in the denture base 82, which prevents accidental fall of the magnetic device 2 or the sleeve 4 from the denture base 82 during use.

Figure 13:
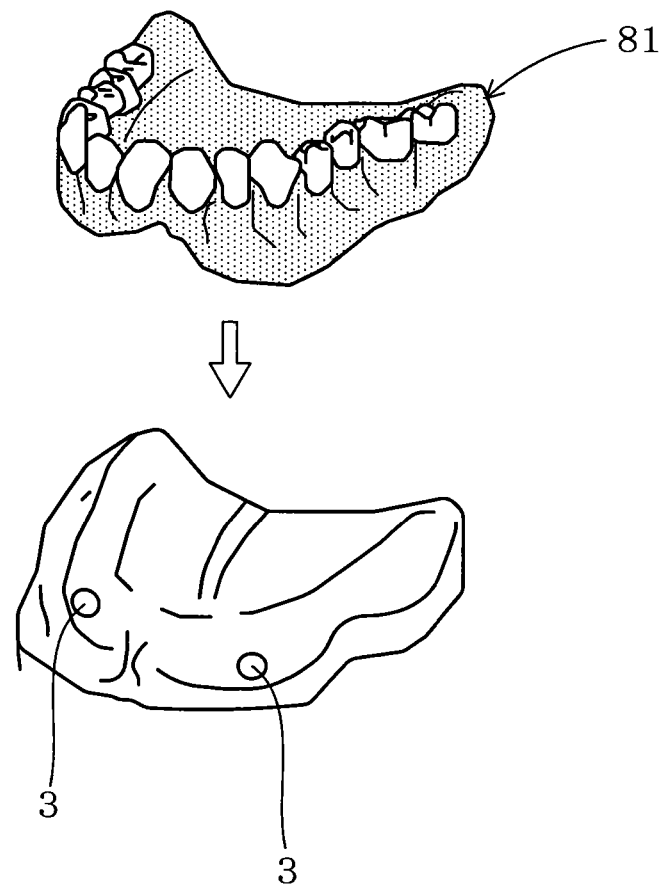
FIG. 13 is an illustration of an example of a denture structure according to the embodiment 1.

FIG. 13 illustrates an example of the denture 81 where the denture attachment 1 according to the embodiment is used. The keeper 3 set in the implant is provided at two positions in the mouth. The denture 81 is formed by embedding the magnetic device 2 mounted with the sleeve 4 at a position corresponding to the position of the keeper 3. The denture 81 may be formed in various shapes that have been conventionally adopted.

As described so far, the denture attachment 1 according to the embodiment effectively succeeds in reducing the lateral force and preventing the denture from being accidentally disengaged, taking advantage of characteristics of the flexible sleeve 4. Further, replacement of the sleeve with a new one to maintain such great advantages can be easily handled during dental treatments.

The invention claimed is:

1. A denture attachment, comprising:
    a magnetic device provided in a denture base and having a permanent magnet embedded therein to exert magnetic attractive force; and
    a keeper made of a soft magnetic material and provided in an abutment, wherein:
    the magnetic device and the keeper are configured to be abutted and joined to each other by the magnetic attractive force;
    the magnetic device includes a cylindrical portion having a cylindrical outer shape and provided with the attractive surface for the keeper in a top end of the cylindrical portion, and a flange portion projected radially outward in a rear end of the cylindrical portion, opposite the top end;
    the cylindrical portion is mounted with a flexible sleeve having elastic deformability and is formed in a cylindrical shape;
    the sleeve is removably mounted to the cylindrical portion by relative movement in the axial direction of the cylindrical portion;
    the sleeve has an outer peripheral concavo-convex portion projected radially outward or dented radially inward on an outer peripheral surface, an axial length longer than the cylindrical portion such that, when the sleeve is positioned on the cylindrical portion to abut the flange portion, one end part of the sleeve projects axially beyond the attractive surface of the magnetic device, in a direction away from the flange portion, to define a keeper housing recess covering part of the keeper when the magnetic device and the keeper are abutted and joined to each other at the attractive surface by the magnetic attractive force;
    the sleeve is configured to be axially applied to and removed from the top end of the cylindrical portion.

2. The denture attachment according to claim 1, wherein:
    the cylindrical portion of the magnetic device has a tapered section in a top end-side outer peripheral part of the cylindrical portion, the tapered section being diametrically reduced toward the attractive surface; and the sleeve has a chamfered section in an inner peripheral corner part of the one end part.

3. The denture attachment according to claim 2, wherein:
the keeper has an outer diameter larger than an outer diameter of the cylindrical portion; and
the sleeve has a base section covering an outer peripheral surface of the cylindrical portion while having the one end part abutted on the flange portion, and a projection where the keeper housing recess is formed, the projection having an inner diameter larger than an inner diameter of the base section.

4. The denture attachment according to claim 3, wherein the keeper is provided in a top end of an implant to be embedded in a jawbone.

5. The denture attachment according to claim 2, wherein the keeper is provided in a top end of an implant to be embedded in a jawbone.

6. The denture attachment according to claim 1, wherein:
the keeper has an outer diameter larger than an outer diameter of the cylindrical portion; and
the sleeve has a base section covering an outer peripheral surface of the cylindrical portion while having the one end part abutted on the flange portion, and a projection where the keeper housing recess is formed, the projection having an inner diameter larger than an inner diameter of the base section.

7. The denture attachment according to claim 6, wherein the keeper is provided in a top end of an implant to be embedded in a jawbone.

8. The denture attachment according to claim 1, wherein the keeper is provided in a top end of an implant to be embedded in a jawbone.

* * * * *